United States Patent [19]
Enloe

[11] Patent Number: 4,753,646
[45] Date of Patent: Jun. 28, 1988

[54] DIAPER WITH WAIST FLAPS

[75] Inventor: Kenneth M. Enloe, Neenah, Wis.

[73] Assignee: Kimberly-Clark Corporation, Neenah, Wis.

[21] Appl. No.: 10,071

[22] Filed: Feb. 2, 1987

Related U.S. Application Data

[63] Continuation of Ser. No. 617,051, Jun. 4, 1984.

[51] Int. Cl.$^4$ ............................................. A61F 13/16
[52] U.S. Cl. ............................... 604/385 R; 604/378; 604/389; 604/385 A
[58] Field of Search ............... 604/378, 385 R, 385 A, 604/389, 393, 394, 397, 398

[56] References Cited

U.S. PATENT DOCUMENTS 3,658,064 4/1972 Pociluyko .................. 604/385.2
4,490,148 12/1984 Beckeström .................. 604/385

FOREIGN PATENT DOCUMENTS 0476600 1/1938 United Kingdom .
0667483 3/1952 United Kingdom .
0833254 4/1960 United Kingdom .
2161059 1/1986 United Kingdom .

Primary Examiner—C. Fred Rosenbaum
Assistant Examiner—Denise Whelton
Attorney, Agent, or Firm—John L. Chiatalas

[57] ABSTRACT

A disposable diaper with at least one flap of fluid pervious material extending along the waist is provided. The flap provides a barrier for feces.

6 Claims, 1 Drawing Sheet

DIAPER WITH WAIST FLAPS

This is a continuation of co-pending application Ser. No. 617,051 filed on June 4, 1984.

FIELD OF THE INVENTION

This invention relates to a disposable diaper and particularly to a diaper having containment flaps.

BACKGROUND OF THE INVENTION

Disposable diapers have become increasingly popular in recent years and have incorporated many features which enhance both comfort and function. Elastic leg diapers have become popular because the use of elastic around the legs of a baby tend to prevent urine and feces leakage in that area.

Babies, and particularly young infants, often have extremely loose explosive bowel movements which while substantially contained at the edge due to the force and volume, as well as the liquidity of consistency can run over both the front and back portions of the waist of the diaper. The introduction of elastic in the waist area will generally inhibit the leakage over the ends of the diaper, however, due to the necessity for maintaining the comfort of the baby elastic which is designed to fit more loosely is used. The gathers in the diaper liner formed by the elastic can, because of the loose fit when compared to the legs, provide channels for fecal escape.

The concept of utilizing waist elastic is disclosed e.g. in U.S. Pat. Nos. 3,990,450 and 3,951,150 in the rather complicated constructions depicted in these two patents, the constringent elastic means are attached in a bow-shaped extended FIG. 8 configuration and a flap is formed by folding over the extended waist ends of the diaper. U.S. Pat. No. 3,930,501, while not disclosing an elasticized waist also has a flap at the ends of the diaper forming the waist portion. In each of these prior art patents the flap is formed by folding the extended ends of the diaper which would conventionally form the waist portion over on itself so that the nonporous fluid impermeable baffle produces a non-porous plastic surface in contact with the baby's waist area. This will quite obviously produce discomfort in the form of abrasive chafing or moisture derived skin irritation.

SUMMARY OF THE INVENTION

According to this invention a diaper is provided in which at least one flap is attached to the end portion of the diaper designed to form the waist with the flap forming a waste containment pocket. In one embodiment, fluid permeable material is used and the pocket is primarily directed toward fecal containment. The fluid permeable material allows for the dissipation of moisture either from perspiration or urine and provides the soft finish associated with the diaper liner which is in contact with the baby's skin in other areas of the diaper.

This flap which extends downward toward the crotch area of the diaper from the end portion preferably is elasticized near the bottom most edge of the downward extending portion. In a particularly preferred embodiment, a flap is positioned at each end of the diaper which forms the waist with constringent means present near the bottom portion of each flap. This combination provides for waste containment generally completely around the waist area and also for increased conformity to the baby due in part to the presence of elastic both in the front and rear portions.

DETAILED DESCRIPTION OF THE INVENTION AND DRAWINGS

Figure 1:
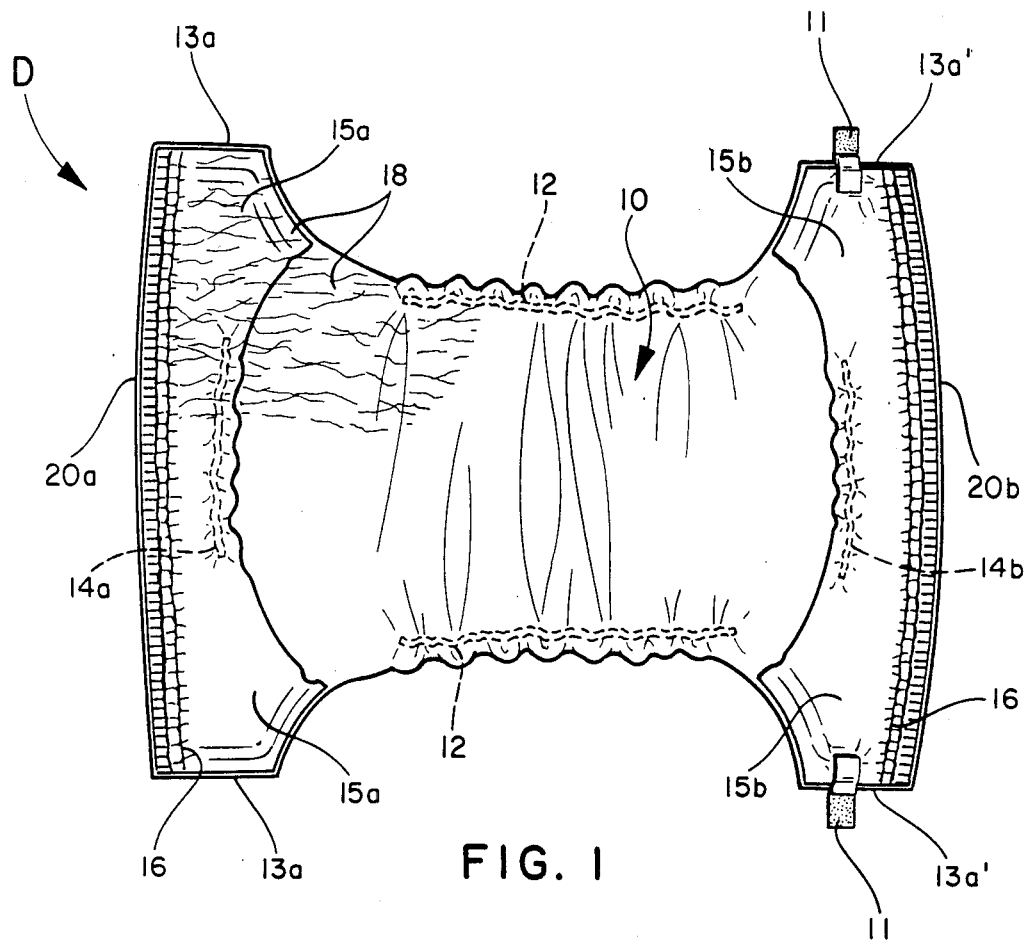
Figure 2:
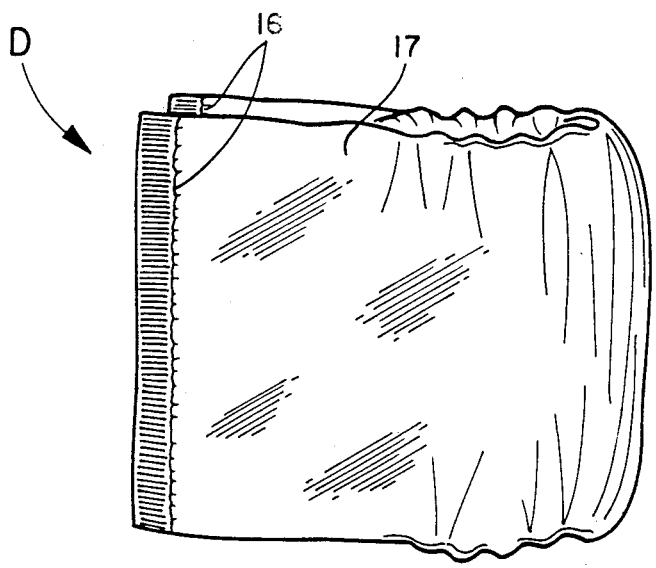

The invention can more readily be understood by reference to the drawings in which FIG. 1 is a plan view of the currently preferred embodiment of this invention which is open prior to use and FIG. 2 is a plan view of the diaper in its folded configuration.

The diaper D has a fluid impervious backing 17 which, as shown in FIG. 2, it is designed to be positioned on the diaper's exterior portion. The liner 18 is adjacent the baby's skin as can be seen by reference to FIG. 1. An absorbant batt (not shown) is positioned between the liner and the backing. The diaper D of this invention has a crotch area 10 which preferably has added absorbant. The crotch area 10 is bordered on either side by elastic 12 which defines a leg area so that when the diaper is worn by the baby a complete ring of elastic is formed around the baby's legs. When diaper is worn it is folded in the crotch area and attached at the waist area formed by diaper ends 20a and 20b by means of tab 11 as is well known in the art. In the particular, currently preferred embodiment depicted in FIG. 1, flaps 15a and b are attached to the end portions 20a and 20b either by heat sealing or adhesively and extend downward and inward. These flaps, made of comformable fluid pervious material, form the fecal barrier referred to above. According to this embodiment, elastic constringent means 14a and 14b are centrally disposed near the unattached inward-positioned edge of each of these flaps.

As can be seen in FIG. 1, ear portions 13a and a' extend outward from the waist end portions 20a and 20b on each side so that the diaper D is laid flat and the elastic 14a and b in the waist area is stretched to allow for the flat profile, a rectangle with four essentially symmetrical lobes extending therefrom at each end is formed.

The elastic is generally in at least a partially relaxed state as it extends into each of the ear areas. The flap is preferably coterminous with the outer edges of the ear. The stretchable portion of the elastic present above and below the crotch area is extensible. The resultant profile is one in which the ears tend to extend in a direction normal to the plane of the diaper ends 20a and 20b.

It has been found that as long as the travel of the elastic when stretched is more than two times the length of the distance between the elastic and the seal which joins the flap to the waist end, the ears when folded inward provide a diaper which is essentially unwrinkled in the cross direction. This can be seen by reference to FIG. 2. A barrier seal line 16 can be added and may in fact be formed by heat sealing of the flap to the diaper end. This barrier line prevents fluid migration from occurring.

The configuration of the diaper of this invention provides a soft, resilient surface for a fecal containment flap as well as a convenient way to introduce waist elastic with minimal irritation.

I claim:
1. A disposable absorbent garment comprising:
   front and back waist areas together defining a waist opening;
   a crotch area disposed between said waist areas;

a pair of elasticized leg areas on either side of said crotch area;

an absorbent composite having opposed longitudinal ends situated adjacent said front and back waist areas, respectively, including a fluid pervious bodyside liner and an essentially coterminous liquid impervious backing with an absorbent batt positioned therebetween; and at least one fluid pervious waste containment pocket formed from or attached to said liner at either of said longitudinal ends of said absorbent composite, said pocket having an upper fixed edge and a free edge positioned inwardly therefrom, defining a pocket opening, including elastic constringent means for partially constraining the effective length of said free edge and maintaining said pocket opening accessible to receive body wastes.

2. The garment according to claim 1 wherein a transversely extending fluid migration barrier strip is positioned along said fixed edge of said pocket.

3. The garment according to claim 1 wherein said constringent means comprises an essentially transversely extending tensioned elasticized member disposed along said pocket opening.

4. The garment according to claim 3 wherein said pocket is formed adjacent at least said rear waist area of said garment.

5. The garment according to claim 3 wherein said garment comprises a generally hourglass shape with a narrowed crotch area, defining opposed pairs of front and rear ear portions engageable with one another about a wearer and wherein said constringent means causes said ear portions to assume a configuration generally perpendicular to the inner surface of said garment, to allow said pocket to receive body wastes, providing conformity and containment about the waist of a wearer.

6. The garment according to claim 5 wherein said constringent means comprises an elastic member and said fixed edge of said pocket is attached to the outer lateral edges of said ears and said elastic member is attached in a relaxed or partially stretched condition to that portion of said pocket overlying said ears and wherein the distance of travel for the unstretched portion of said elastic member when said ears are positioned in the same plane as said inner surface is at least twice the distance between the attachment of said pocket to said ends of said garment and said elastic.

* * * * *